(12) United States Patent
Maragni et al.

(10) Patent No.: US 7,956,042 B2
(45) Date of Patent: Jun. 7, 2011

(54) CRYSTALLINE FORMS OF MACROLIDE COMPOUNDS ENDOWED WITH ANTIINFLAMMATORY ACTIVITY

(75) Inventors: Paolo Maragni, Virgilio (IT); Dario Braga, Bologna (IT); Roberto Brescello, Abano Terme (IT); Livius Cotarca, Cervignano del Friuli (IT); Alessandro Di Maria, Milan (IT); Franco Massaccesi, Grancona (IT); Elisa Melotto, Lonigo (IT); Ivan Michieletto, Venice (IT); Gabriele Morazzoni, Lainate (IT); Mauro Napoletano, Milan (IT); Franco Pellacini, Milan (IT); Angelo Restelli, Gerenzano (IT); Massimo Verzini, Caldiero (IT)

(73) Assignee: Zambon S.p.A., Bresso (IT)

( * ) Notice: Subject to any disclaimer, the term of this patent is extended or adjusted under 35 U.S.C. 154(b) by 558 days.

(21) Appl. No.: 11/994,784

(22) PCT Filed: Jul. 5, 2006

(86) PCT No.: PCT/EP2006/006541
§ 371 (c)(1),
(2), (4) Date: Sep. 26, 2008

(87) PCT Pub. No.: WO2007/003422
PCT Pub. Date: Jan. 11, 2007

(65) Prior Publication Data
US 2009/0018089 A1 Jan. 15, 2009

(30) Foreign Application Priority Data

Jul. 6, 2005 (EP) .................................... 05106123

(51) Int. Cl.
*A61K 31/70* (2006.01)
*C07H 17/08* (2006.01)
(52) U.S. Cl. .......................................... 514/29; 536/7.2
(58) Field of Classification Search .................... 536/7.2
See application file for complete search history.

(56) References Cited

FOREIGN PATENT DOCUMENTS

WO 2004013153 9/2004
WO 2006100195 E 9/2006

OTHER PUBLICATIONS

Borka et al: "Crystal Polymorphism of Pharmaceuticals" Acta Pharmaceutica Jugoslavice, Savez Farmaceutskih Drustava Jugoslavije, Zagreb, YU, vol. 40, 1990, pp. 71-94.

*Primary Examiner* — Elli Peselev
(74) *Attorney, Agent, or Firm* — Lucas & Mercanti, LLP

(57) ABSTRACT

The present invention relates to macrolide compounds endowed with antiinflammatory activity and more particularly relates to new stable crystalline forms of a macrolide derivative with antiinflammatory activity, processes for the preparation of such forms, pharmaceutical compositions containing them as active ingredient and the use of said crystalline forms for the treatment of inflammatory diseases.

17 Claims, 2 Drawing Sheets

Powder X-ray diffractograms of crystalline Form I.

Powder X-ray diffractograms of crystalline Form II.

DSC thermogram of crystalline Form I.

DSC thermogram of crystalline Form II.

CRYSTALLINE FORMS OF MACROLIDE COMPOUNDS ENDOWED WITH ANTIINFLAMMATORY ACTIVITY

This application is a U.S. National stage of PCT/EP2006/006541 filed on Jul. 5, 2006, which claims priority to and the benefit of EP Application No. 05106123.2, filed on Jul. 6, 2005, the contents of which are incorporated herein by reference in their entirety.

The present invention relates to macrolide compounds endowed with antiinflammatory activity and more particularly it relates to new stable crystalline forms of a macrolide derivative with antiinflammatory activity, processes for the preparation of such forms, pharmaceutical compositions containing them as active ingredient and the use of said crystalline forms for the treatment of inflammatory diseases.

It is known that many antibiotics in particular the class of erythromycin based macrolides having 14 ring atoms, have antiinflammatory properties in addition to their antibacterial activity [Cin. Immunother., (1996), 6, 454-464].

Erythromycin is a natural macrolide (The Merck Index, XIII Edition, No. 3714, p. 654) that has been widely used in the treatment of infections caused by Gram-positive bacteria, a number of Gram-negative bacteria and micoplasms.

Recently the interest of the scientific community has turned towards the antiinflammatory and immunomodulatory properties of erythromycin and derivatives thereof [Journal of Antimicrobial Chemotherapy, (1998), 41, Suppl. B, 37-46].

This activity is well documented both in the clinical studies and in in vivo and in vitro experiments.

However, the fact that conventional macrolide compounds have strong antibacterial activity does not allow their broader use in the chronic treatment in inflammatory processes not caused by pathogenic microorganism, since this could give rise to the rapid development of resistant strains.

The above technical problem was successfully solved in the International patent application WO 2004/013153 (WO'153) in the name of the same Applicant, wherein macrolide derivatives endowed with antiinflammatory activity and free of antibiotic activity are described.

In particular, the compound (9S)-3-descladinosil-3'-desmethyl-3'-acetyl-9-deoxo-9-dehydro-erythromycin A (hereinafter the COMPOUND) of formula (I)

is obtained in a solid amorphous form.

The ability of a substance to crystallize with more than one crystal structure is known as polymorphism and a particular crystal form is called polymorph.

WO '153 does not disclose or suggest the possible existence of crystalline polymorph forms of the COMPOUND.

It is known in the art that different solid forms of the same active compound may exhibit distinct physical properties such as solubility, dissolution rate, and/or shelf-life stability, which can lead to differences in efficacy.

In addition, the distinct physical properties of solid forms with respect to the crystalline or amorphous state, may influence markedly the chemical and pharmaceutical manufacturability of a compound, particularly, when it is prepared or used on industrial scale.

For example, it is important to be able to provide drug substances in a form which is as pure as possible.

Typically, amorphous substances are more difficult to handle and to formulate than crystalline forms and are often endowed with stability and impurity problems.

It is therefore desirable for a skilled person to obtain the COMPOUND in a substantially crystalline stable form, which can be easily isolated and make it particularly suitable for use as medicament.

WO'153 provides an efficient method to produce the COMPOUND in an amorphous form starting from erythromycin.

It has now been found that by using suitable reaction conditions and solvents, the COMPOUND can be isolated from the reaction mixture in stable solid crystalline forms, in good yields and purity.

The crystallinity of the polymorphic forms was confirmed by measuring X-ray diffraction of a powder sample.

Therefore, it is an object of the present invention a crystalline stable form of the COMPOUND, which is referred to herein as crystalline Form I.

Crystalline Form I can provide an X-ray powder diffraction pattern substantially in accordance with that shown in FIG. 1.

The 2θ angle values of the diffraction peaks as well as their correspondent relative intensity are reported in the following Table 1:

TABLE 1

| Angle (°2θ) | Intensity (%) |
|---|---|
| 4.9 | 40.2 |
| 5.5 | 13.4 |
| 6.8 | 7.5 |
| 8.5 | 17.7 |
| 9.1 | 100.0 |
| 9.6 | 62.0 |
| 10.0 | 45.1 |
| 10.3 | 79.5 |
| 11.1 | 29.7 |
| 11.6 | 14.9 |
| 12.6 | 20.7 |
| 13.5 | 26.4 |
| 14.0 | 15.9 |
| 14.5 | 56.5 |
| 15.8 | 15.4 |
| 16.2 | 33.9 |
| 16.6 | 26.3 |
| 17.0 | 28.6 |
| 18.2 | 57.3 |
| 19.3 | 31.4 |
| 20.0 | 25.3 |
| 20.9 | 30.5 |
| 21.4 | 26.9 |
| 21.9 | 20.9 |
| 23.3 | 15.9 |
| 23.9 | 16.2 |
| 29.1 | 13.6 |

The crystalline Form I of the COMPOUND is characterized by providing an X-ray powder diffraction pattern comprising 2θ angle values of about 4.9; about 8.5; about 9.1; about 9.6; about 10.3; about 11.1; about 14.5; about 17.0; about 18.2; about 19.3. Crystalline Form I is further characterized by providing a differential scanning calorimetry curve to have an onset of melting which is comprised in the range 163-174° C. (onset: 168.2° C.; peak: 174.8° C.).

Preferably, crystalline Form I provides a differential scanning calorimetry curve to have an onset of melting which is comprised in the range 163-168° C.

Crystalline Form I fulfils more adequately the above mentioned processing and stability requirements than the known solid amorphous form obtained in WO '153. It has also surprisingly been found that the COMPOUND can be obtained in a more stable crystalline form.

Therefore, it is a further object of the present invention a crystalline stable form of the COMPOUND, which is referred to herein as crystalline Form II.

Crystalline Form II can provide an X-ray powder diffraction pattern substantially in accordance with that shown in FIG. 2.

The 2θ angle values of the diffraction peaks as well as their correspondent relative intensity are reported in the following Table 2:

TABLE 2

| Angle (°2θ) | Intensity (%) |
|---|---|
| 6.8 | 5.6 |
| 9.4 | 2.9 |
| 10.0 | 13.2 |
| 11.4 | 15.2 |
| 11.9 | 70.8 |
| 12.9 | 27.9 |
| 13.4 | 91.4 |
| 13.9 | 11.5 |
| 14.6 | 37.4 |
| 15.3 | 42.8 |
| 16.4 | 100.0 |
| 17.4 | 5.8 |
| 18.8 | 34.1 |
| 19.0 | 36.3 |
| 19.5 | 29.6 |
| 19.8 | 10.5 |
| 20.2 | 16.3 |
| 20.5 | 18.4 |
| 21.1 | 24.1 |
| 21.5 | 17.1 |
| 21.9 | 12.7 |
| 22.7 | 17.7 |
| 23.2 | 14.3 |
| 24.0 | 14.1 |
| 24.2 | 10.3 |
| 38.1 | 7.6 |
| 38.8 | 5.8 |

The crystalline Form II of the COMPOUND is characterized by providing an X-ray powder diffraction pattern comprising 2θ angle values of about 11.9; about 13.4; about 13.9; about 14.6; about 15.3; about 16.4; about 17.4; about 18.8; about 19.0; about 19.5; about 21.1; about 22.7.

Form II is further characterized by providing a differential scanning calorimetry curve to have an onset of melting which is comprised in the range 218-226° C. (onset: 222.7° C.; peak: 225.0° C.).

Preferably, crystalline Form II provides a differential scanning calorimetry curve to have an onset of melting which is comprised in the range 218-223° C.

Crystalline Form II is characterized by low thermodynamic activity, thus exhibiting advantageous properties such as being thermodynamically more stable than crystalline Form I, especially in biological fluids.

Crystalline Form II is isolated from the reaction mixture by processes conveniently applicable on industrial scale, with good yields and purity and, as a result of its termodynamical stability, it is particularly suitable for use as medicament.

According to the invention there is further provided a process for the preparation of crystalline Form I by isolating the product in accordance with an antisolvent precipitation process.

In WO '153, second synthesis route, the preparation of the COMPOUND was carried out starting from erythromycin A by reduction of the keto group in position 9, mono-demethylation of the nitrogen atom in position 3', hydrolysis of cladinose and acetylation of the obtained amine.

At the end of the acetylating step, the dry residue of the COMPOUND was dissolved in ethyl acetate and impurities were washed by a diluted citric acid solution.

The so obtained organic phase was filtered and the solvent distilled.

In order to isolate the desired crystalline Form I, methyl-tert-butyl ether is added as antisolvent to a solution of the COMPOUND in ethyl acetate.

Therefore, it is a further object of the present invention a process for the preparation of crystalline Form I, which comprises: addition of methyl-tert-butyl ether to a solution of the COMPOUND in ethyl acetate, cooling the reaction mixture obtained, filtering and drying the crystallized product.

For example, the preparation of the crystalline Form I is carried out by adding methyl-tert-butyl ether as antisolvent to the solution resulting from the dissolution in ethyl acetate of the dry residue of the COMPOUND obtained following the procedure described in WO '153.

Alternatively, the mixture solvent/antisolvent containing the COMPOUND, i.e. the mixture comprising ethyl acetate/methyl-tert-butyl ether, is obtained by adding methyl-tert-butyl ether to the COMPOUND solution directly coming from the acetylation step.

In other words, the solution of the COMPOUND preferred as starting material in the antisolvent precipitation is the reaction mixture directly coming from the work-up of the acetylation step.

Preferably, the weight ratio between ethyl acetate and methyl-tert-butyl ether is around 1:1 w/w.

Preferably, the addition of the antisolvent is carried out at a temperature of about 50° C.

Preferably, the ethyl acetate solution has a product concentration around 30-40% by weight.

Preferably, the mixture is cooled over a time of 3 hours according to a process which foresees lowering temperature 0.08° C./minute up to about 10° C.

A practical embodiment of the process object of the present invention comprises the distillation of the ethyl acetate solution till a product concentration of 30-40% by weight is reached, keeping under slow stirring at room temperature. The product starts precipitating and the suspension is heated till around 50° C., methyl-tert-butyl ether is then added and after about 3 hours the reaction mixture is cooled up to about 10° C. The solid is filtered, washed with ethyl acetate/methyl-tert-butyl ether 1/1 and dried under vacuum. The product is isolated as crystalline Form I.

According to the invention there is further provided a process for the conversion of crystalline Form I into a more stable crystalline Form II.

Therefore, it is a a further object of the present invention a process for the preparation of crystalline Form II, which comprises the conversion from crystalline Form I to crystalline Form II by heating a water suspension of said crystalline Form I. Preferably, the weight ratio water/substrate is around 15:1 w/w in order to improve the reologic properties of the suspension and avoid stirring and filtration drawbacks that may occur.

Preferably, the suspension is heated up to a temperature comprised between 30 and 35° C.

A practical embodiment of the process object of the present invention comprises heating a suspension of crystalline Form I in water up to a temperature around 30-35° C., keeping under stirring for about one day at the same temperature, cooling to room temperature, filtering the reaction mixture, washing with water and drying under vacuum. The product is isolated as crystalline Form II.

According to the invention there is further provided a process for the preparation of the thermodynamically stable crystalline Form II by avoiding the isolation of the kinetic crystalline Form I and the subsequent conversion therefrom.

It has now been found that it is possible to induce the direct precipitation of the thermodynamic crystalline Form II by crystallization from methyl ethyl ketone.

Therefore, it is a further object of the present invention a process for the preparation of crystalline Form II which comprises the crystallization of the COMPOUND from methyl ethyl ketone.

For example, the preparation of the crystalline Form II is carried out by crystallising the solution resulting from the dissolution in methyl ethyl ketone of the dry residue of the COMPOUND obtained following the procedure described in WO '153.

Alternatively, the solution of the COMPOUND in methyl ethyl ketone, preferred as starting product in the crystallization object of the invention, is the reaction mixture directly coming from the work-up of the acetylating step upon change of solvent from ethyl acetate to methyl ethyl ketone according to conventional methods. Preferably, the solution of the COMPOUND in methyl ethyl ketone comprises a residual amount of ethyl acetate lower than 15% by weight.

Preferably, the solution of the COMPOUND in methyl ethyl ketone is concentrated till a product concentration comprised between 25-50% by weight is reached.

More preferably, the solution is concentrated till a product concentration around 36% by weight is reached.

It may be useful to seed with crystalline Form II in order to facilitate the product precipitation.

Preferably, the solution is seeded at room temperature before distilling till obtaining a concentration of the solution suitable for the precipitation of crystalline Form II.

Preferably, when said suitable concentration is reached and the product starts precipitating, the obtained suspension is maintained for some hours at a temperature of about 75° C.

Preferably, the mixture is cooled up to about 0° C. over a time of 5 hours and it is maintained at that temperature for about 1 hour.

A practical embodiment of the process object of the present invention comprises the dissolution of the COMPOUND, obtained in solid amorphous Form as described in WO '153, in methyl ethyl ketone.

The solution is distilled till obtaining a product concentration around 36% by weight.

After cooling up to around 75° C. the reaction mixture is kept under stirring for some hours. Then it was cooled till 0° C. over a time of 5 hours and is maintained at that temperature for about 1 hour. The mixture is filtered and washed with methyl ethyl ketone. The product is isolated as crystalline Form II.

An alternative practical embodiment of the process object of the present invention comprises the change of solvent, from ethyl acetate to methyl ethyl ketone, of the reaction mixture coming from the work up of the acetylating step. After filtering and washing with methyl ethyl ketone, the solution is seeded with crystalline Form II and the mixture is distilled till obtaining a product concentration around 36% by weight. After cooling up to around 75° C. the reaction mixture is kept under stirring for some hours. Then it was cooled till 0° C. over a time of 5 hours and is maintained at that temperature for about 1 hour. The mixture is filtered and washed with methyl ethyl ketone. The product is isolated as crystalline Form II.

The skilled person will realise how the crystallizzation process from methyl ethyl ketone, object of the invention, is also useful for the preparation of crystalline Form II starting from crystalline Form I.

The compounds object of the present invention are antiinflammatory macrolides lacking antibiotic activity and are therefore useful in the treatment and prophylaxis of inflammatory diseases.

Therefore, a further object of the present invention is the use of said COMPOUND in its crystalline Form I as a medicament.

A further object of the present invention is the use of said COMPOUND in its crystalline Form II as a medicament.

The compounds of the present invention for their therapeutic or preventive use in the above mentioned pathologies will be preferably used in a pharmaceutical composition suitable for the oral, rectal, sublingual, parenteral, topical, transdermal and inhalatory administration.

Therefore, another object of the present invention is a pharmaceutical composition comprising a therapeutically effective amount of the COMPOUND in crystalline Form I as active ingredient in admixture with a pharmaceutically acceptable carrier.

Another object of the present invention is pharmaceutical composition comprising a therapeutically effective amount of the COMPOUND in crystalline Form II as active ingredient in admixture with a pharmaceutically acceptable carrier.

The pharmaceutical compositions object of the present invention may be liquid, suitable for the oral and/or parenteral administration such as, for example, drops, syrups, solutions, injectable solutions ready to use or prepared by the dilution of a lyophilized preparation, and solid or semisolid such as tablets, capsules, granulates, powders, pellets, vaginal suppositories, suppositories, creams, ointments, gels, unguents; or still solutions, suspensions, emulsions, and other Forms suitable for the inhalatory or transdermal administrations.

Depending on the type of composition, besides a therapeutically effective amount of the compounds object of the invention, they will contain some solid or liquid excipients or diluents for pharmaceutical use and optionally further additives, commonly used in the preparation of pharmaceutical compositions, such as thickeners, binders, lubricants, disintegrators, flavouring and colouring agents.

The preparation of the pharmaceutical compositions object of the invention can be carried out according to common techniques.

The invention is illustrated by reference to the accompanying drawings described below.

Figure 1:
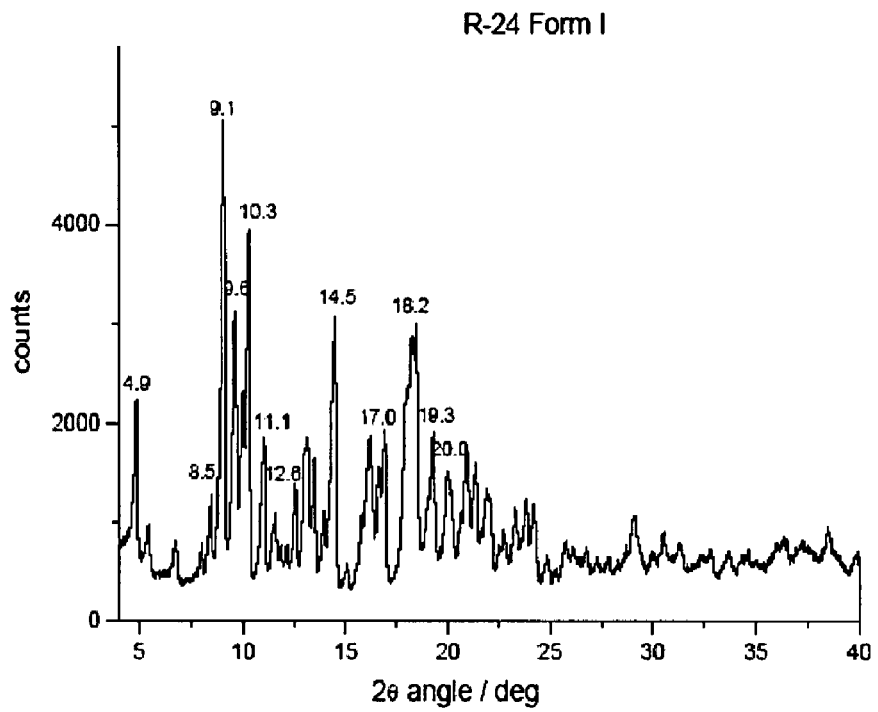
FIG. 1 shows powder X-ray diffractograms of crystalline Form I.

The DSC thermograms were determined on TA Q100 (10° C./min; Aluminium pan)

The onset of melting is defined as the point at which a significant change from the baseline occurs and was measured.

The skilled person will realise that the precise value of the melting point will be influenced by the purity of the compound, the sample weight, the heating rate and the particle size.

The X-ray diffractograms of crystalline Form I and II of the present invention were measured on X'Pert Philips (Bragg-Brentano geometry) X-ray diffractometer with Cu K alpha-1 radiation source.

The position and intensity of peaks were measured using the program X' Pert Philips Analitycal.

The relative intensity of the X-ray powder diffraction peaks can vary depending upon sample preparation technique, sample mounting procedure and the particular instrument employed.

It is to be understood that while the invention is described in conjunction of the preferred embodiments thereof, those skilled in the art are aware that other embodiments could be made without departing from the spirit of the invention.

For better illustrating the invention the following examples are provided.

EXAMPLE 1

Preparation of (9S)-3-descladinosil-3'-desmethyl-3'-acetyl-9-deoxo-9-dehydro-erythromicin A Crystalline Form I The COMPOUND (26.0 g) in solid amorphous form, obtained from the work up of the acetylating step according to what described in WO'153, was dissolved in ethyl acetate (39.0 g). The mixture was stirred for 2 hours at room temperature, the product starts precipitating and the obtained suspension was heated up to around 50° C. Methyl-tert-butyl ether (39.0 g) was then added over 30 minutes and the suspension was stirred for 2 hours at 50° C., then cooled to 10° C. in 8 hours and kept for further 2 hours under stirring at this temperature.

The resulting solid was isolated by filtration washing with a mixture of ethyl acetate/methyl-tert-butyl ether (1:1) (3×5 ml) and then dried under vacuum at 45° C. over 16 hours to give crystalline Form I (14.4 g) as a white solid.

EXAMPLE 2

Conversion of Crystalline Form I into Crystalline Form II

A suspension of crystalline Form I (55.4 g, 0.098 moles) in demineralized water 898.5 g was heated up to 30-35° C. and maintained under stirring for at least 24 hours at that temperature.

The conversion was considered complete when the DSC profile shows a single peak and the onset temperature was $\geq 219.0°$ C.

The suspension was then cooled up to 25° C. over a time of 30 minutes and maintained at room temperature for 1 hour.

The solid was filtered on gooch and the panel was washed with demineralized water (60.0 g).

The solid was dried at 50° C. under vacuum to give crystalline Form II (52.4 g, titre 96.9%, yield 92.7%).

EXAMPLE 3

Preparation of (9S)-3-descladinosil-3'-desmethyl-3'-acetyl-9-deoxo-9-dehydro-erythromicin A Crystalline Form II The COMPOUND (126.7 g) obtained according to what described in WO'153 was dissolved in methyl-ethyl ketone (1586.0 g). The so obtained solution was distilled at normal pressure up to a concentration of about 15-17% w/w, then seeded and further distilled up to a final concentration of about 25-26% w/w. The resulting suspension was stirred at 75° C. over 5 hours, cooled to 0° C. over 7.5 hours (about 10° C./h) and kept at this temperature for further 2 hours under stirring. The resulting solid was isolated by filtration washing with cold (0° C.) methyl-ethyl ketone (2×56 g) and then dried under vacuum at 50° C. over 16 hours to give crystalline Form II (110.2 g) as a white solid.

The invention claimed is:

1. Crystalline Form I of a compound of formula

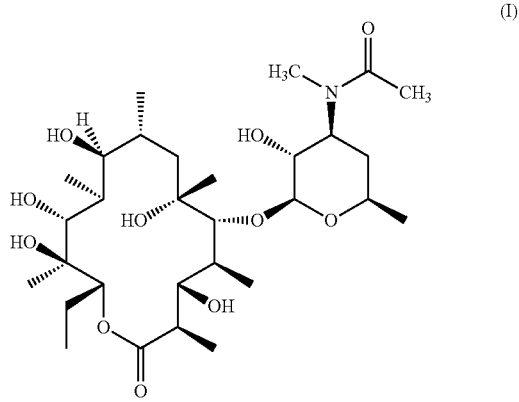

(I)

characterized by an X-ray powder diffraction pattern comprising 2θ angle values of about 4.9; about 8.5; about 9.1; about 9.6; about 10.3; about 11.1; about 14.5; about 17.0; about 18.2; about 19.3.

2. A crystalline form according to claim 1 which provide an X-ray powder diffraction pattern substantially in accordance with that shown in FIG. 1.

3. A crystalline form according to claim 1 characterized by a differential scanning calorimetry curve to have an onset of melting which is comprised in the range 163-174° C.

4. A crystalline form according to claim 3 characterized by a differential scanning calorimetry curve to have an onset of melting which is comprised in the range 163-168° C.

5. Crystalline Form II of the compound of formula I

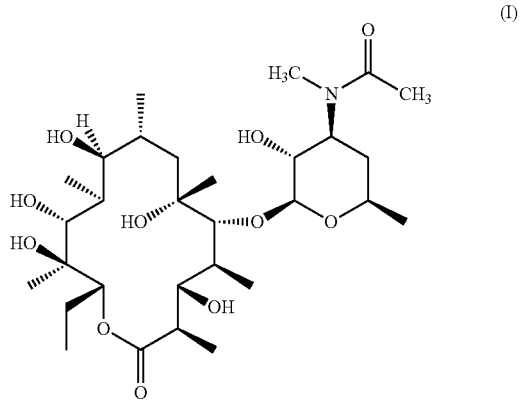

(I)

characterized by an X-ray powder diffraction pattern comprising 2θ angle values of about 11.9; about 13.4; about 13.9; about 14.6; about 15.3; about 16.4; about 17.4; about 18.8; about 19.0; about 19.5; about 21.1; about 22.7.

Figure 2:
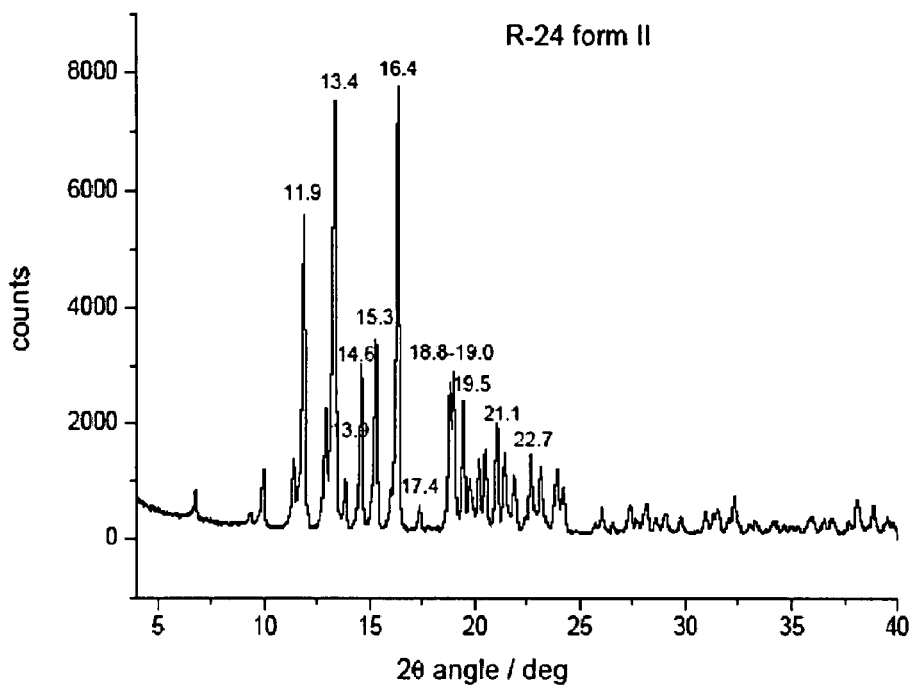
FIG. 2 shows powder X-ray diffractograms of crystalline Form II.
Figure 3:
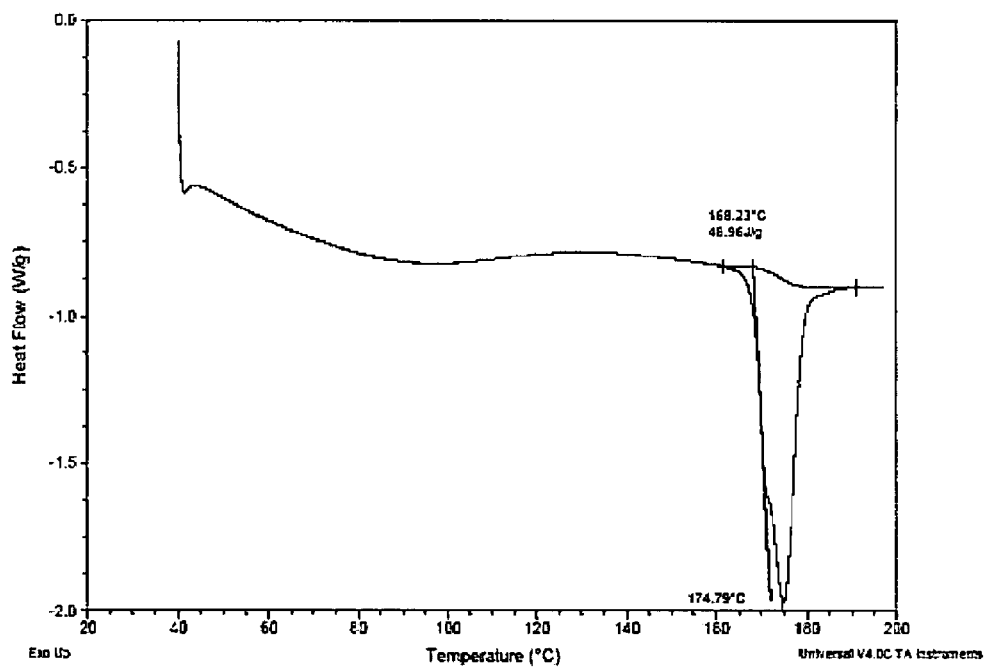
FIG. 3 shows DSC thermogram of crystalline Form I.
Figure 4:
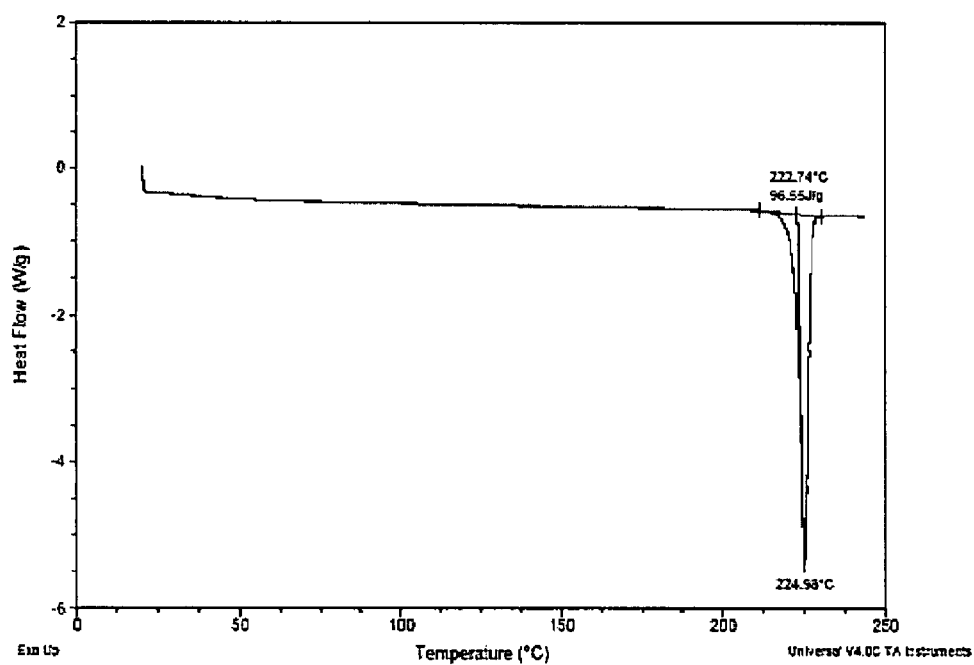
FIG. 4 shows DSC thermogram of crystalline Form II.

6. A crystalline form according to claim 5 which provide an X-ray powder diffraction pattern substantially in accordance with that shown in FIG. 2.

7. A crystalline form according to claim 5 characterized by a differential scanning calorimetry curve to have an onset of melting which is comprised in the range 218-226° C.

8. A crystalline form according to claim 7 characterized by a differential scanning calorimetry curve to have an onset of melting which is comprised in the range 218-223° C.

9. A process for the preparation of crystalline Form I of a compound of formula I

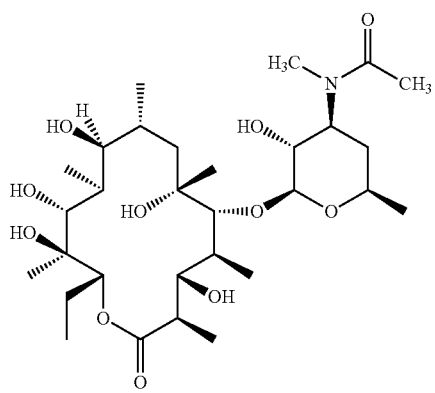
(I)

which comprises: addition of methyl-tert-butyl ether to a solution of the compound of formula I in ethyl acetate, cooling the reaction mixture obtained, filtering and drying the crystallized product.

10. A process for the preparation of crystalline Form II of a compound of formula I

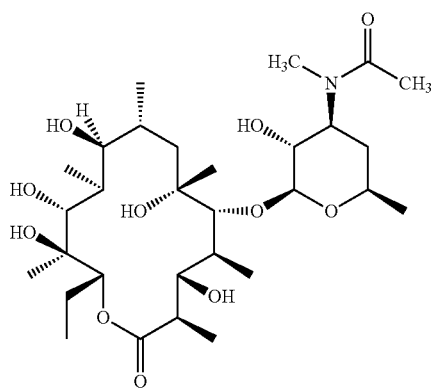
(I)

which comprises the conversion from crystalline Form I of the compound of formula I to crystalline Form II by heating a water suspension of said crystalline Form I of the compound of formula I.

11. A process according to claim 10 wherein the suspension is heated up to a temperature comprised between 30 and 35° C.

12. A process for the preparation of crystalline Form II of a compound of formula

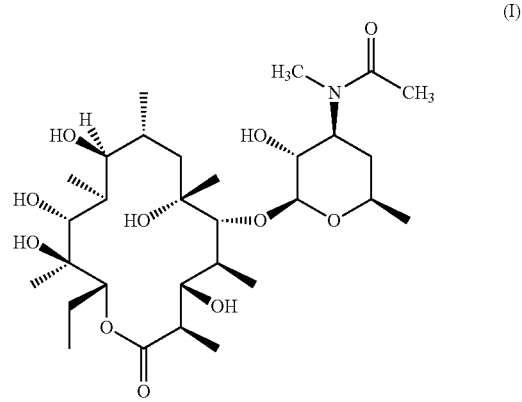
(I)

which comprises the crystallization of the compound of formula I from methyl ethyl ketone.

13. A process according to claim 12 further comprising seeding the solution with crystalline Form II.

14. A solid pharmaceutical composition comprising a therapeutically effective amount of crystalline Form I as claimed in claim 1 as active ingredient in admixture with a pharmaceutically acceptable carrier.

15. A solid pharmaceutical composition comprising a therapeutically effective amount of crystalline Form II as claimed in claim 5 as active ingredient in admixture with a pharmaceutically acceptable carrier.

16. A lyophilized pharmaceutical composition comprising a therapeutically effective amount of crystalline Form I as claimed in claim 1 as active ingredient in admixture with a pharmaceutically acceptable carrier.

17. A lyophilized pharmaceutical composition comprising a therapeutically effective amount of crystalline Form II as claimed in claim 5 as active ingredient in admixture with a pharmaceutically acceptable carrier.

* * * * *